(12) United States Patent
Manohar et al.

(10) Patent No.: US 9,706,977 B2
(45) Date of Patent: Jul. 18, 2017

(54) IMAGING APPARATUS AND METHOD

(75) Inventors: Srirang Manohar, Haaksbergen (NL); Antonius Gerardus Johannes Maria van Leeuwen, Bussum (NL)

(73) Assignee: P A Imaging Holding B.V., Enshede (NL)

( * ) Notice: Subject to any disclaimer, the term of this patent is extended or adjusted under 35 U.S.C. 154(b) by 2055 days.

(21) Appl. No.: 12/519,659

(22) PCT Filed: Dec. 21, 2007

(86) PCT No.: PCT/NL2007/050698
§ 371 (c)(1),
(2), (4) Date: Oct. 21, 2009

(87) PCT Pub. No.: WO2008/075961
PCT Pub. Date: Jun. 26, 2008

(65) Prior Publication Data
US 2010/0041987 A1    Feb. 18, 2010

(30) Foreign Application Priority Data

Dec. 21, 2006  (EP) ..................................... 06077300

(51) Int. Cl.
*A61B 8/00* (2006.01)
*A61B 8/08* (2006.01)
(Continued)

(52) U.S. Cl.
CPC .............. *A61B 8/08* (2013.01); *A61B 5/0095* (2013.01); *G01N 29/0672* (2013.01);
(Continued)

(58) Field of Classification Search
None
See application file for complete search history.

(56) References Cited

U.S. PATENT DOCUMENTS 5,596,989 A * 1/1997 Morita .......................... 600/437
2003/0225320 A1 * 12/2003 Jeon et al. .................... 600/310

OTHER PUBLICATIONS

Hoelen et al. "Three dimensional photo acoustic imaging of blood vessels in the tissue", Optics Letters vol. 23, No. 8, pp. 648-650, Apr. 15, 1998.*

(Continued)

*Primary Examiner* — Joseph M Santos Rodriguez
(74) *Attorney, Agent, or Firm* — The Watson IP Group, PLC; Vladan M. Vasiljevic; Lawrence J. Chapa

(57) ABSTRACT

A thermoacoustic imaging apparatus comprises an electromagnetic radiation source, an acoustic signal detection probe and a radiation responsive acoustic signal generator outside the sample area. The detection probe arrangement detects both signals generated in the sample area in response to the electromagnetic irradiation and an acoustic signal from the radiation responsive acoustic signal generator that has traveled through the sample area. An acoustic transmission parameter such as a speed of sound or absorption as a function of a position in the sample area is computed from signals due to the radiation responsive acoustic signal generator. The acoustic transmission parameter is used to correct the computation of a thermoacoustic image from detections due to acoustic signals generated in the sampled area.

20 Claims, 2 Drawing Sheets

(51) Int. Cl.
*A61B 5/00* (2006.01)
*G01N 29/06* (2006.01)
*G01N 29/22* (2006.01)
*G01N 29/24* (2006.01)

(52) U.S. Cl.
CPC ....... *G01N 29/228* (2013.01); *G01N 29/2418* (2013.01); *A61B 8/4281* (2013.01); *G01N 2291/011* (2013.01); *G01N 2291/015* (2013.01); *G01N 2291/0237* (2013.01)

(56) References Cited

OTHER PUBLICATIONS

Xing et al. "Correction of the effects of acoustic heterogeneity on thermoacoustic tomography using transmission ultrasound tomography", Proceedings SPIE vol. 6086, pp. 60860W1-60860W5, Jan. 2006.*

\* cited by examiner

IMAGING APPARATUS AND METHOD

FIELD OF THE INVENTION

The invention relates to an imaging apparatus and method and in particular to an apparatus and method that may be used for thermoacoustic imaging.

BACKGROUND

Thermoacoustic imaging (also called photoacoustic or optoacoustic imaging) is known for example from U.S. Pat. Nos. 5,840,023 and 5,713,356. Thermoacoustic imaging of tissue involves application of a short pulse of electromagnetic radiation to tissue and detection of acoustic waves emitted by absorbing structures within the tissue in response to the electromagnetic pulse. As used herein the term "acoustic" encompasses ultrasound, human audible sound, or infrasound and our combinations thereof; all these will also be referred to as sound. An electromagnetic radiation pulse causes abrupt heating and consequently localized temperature rise followed by thermal expansion at positions of radiation absorption, which results in generation of acoustic pulses from these positions. This is the photoacoustic effect.

The time of reception of the acoustic pulses at an acoustic detector, coupled acoustically to the tissue, is dependent on the distance between the sites of acoustic pulse generation and the detector. Thus acoustic detection at a single location can be used to determine the strength of the acoustic sources in the tissue at different distances. Detection of the acoustic pulses at a plurality of locations allows for the reconstruction in two- or three-dimensions of thermoacoustic images which are images of a measure of electromagnetic absorptivity of the tissue.

The reconstruction of such images requires knowledge of the speed of sound in the tissue to convert temporal resolution (or temporal phase resolution) into spatial resolution. In US patent application No. 2005/277834 a position independent speed of sound is used. Use of a position dependent speed of sound is described in an article titled "Correction of the effects of acoustic heterogeneity on thermoacoustic tomography using transmission ultrasound tomography" by Xin Jin, Lihong V. Wang and published in the 7$^{th}$ Conference on Biomedical Thermoacoustics, Optoacoustics and Acousto-optics, (Editor A. A. Oraevsky), Proceedings SPIE Vol 6086 6086W-32.

Wang proposes to use an additional measurement to the thermoacoustic experiment to measure the spatial variation of the speed of sound. This is an ultrasound transmission tomographic measurement. An ultrasound transmitter is used in addition to the acoustic receiver of the thermoacoustic experiment. From measurements of the arrival time of acoustic pulses generated by the transmitter through the sample in water, compared with the arrival time of acoustic pulses without the sample, the speed of sound is estimated. This measurement is performed taking projections around the sample. A speed of sound tomogram is generated using standard reconstruction concepts from x-ray computed tomography. The obtained spatial variations of the speed of sound are used to correct the thermoacoustic image instead of using a spatially independent single speed of sound. A disadvantage of the technique of Wang is that it requires a separate acoustic transmitter and a separate measurement.

From US2003/0167002 it is known to investigate the thermal effects of radiation on tissue by observing resulting changes in the speed of sound. However, this document does not concern thermoacoustic imaging.

Another acoustic transmission property that may affect the reliability of thermoacoustic images is position dependent attenuation of sound in the sample.

SUMMARY OF THE INVENTION

Among others, it is an object to provide for a method and apparatus for imaging wherein an acoustic transmission parameter of a sample can be obtained with little overhead in an apparatus suitable for forming thermoacoustic images.

In an embodiment, it is an object to provide for a method and apparatus for improving thermoacoustic imaging.

An imaging apparatus according to claim 1 is provided. Herein radiation travels along a path to a sample that generates acoustic signals. In this path a radiation responsive acoustic generator is provided outside the sample. The acoustic signal generated by the radiation responsive acoustic generator subsequently travels through the sample.

Acoustic signals received from the radiation responsive acoustic generator after their travel through the sample are identified and used to estimate an acoustic transmission parameter, such as the speed of sound or acoustic attenuation as a function of position in the sample area.

In an embodiment the irradiation is in the form of light pulses but other types of radiation may be used. In an embodiment a carbon fibre is used as a radiation responsive acoustic generator, but any other material with properties of radiation absorption that generates acoustic signals by the photoacoustic effect in response to irradiation may be used, such as coloured nylon fibre (colored to absorb light form the radiation source), or a strand of black human or animal hair. In an embodiment the radiation responsive acoustic generator has a small cross-section compared to the cross-section of the irradiation so that only a small fraction of the incident irradiation is absorbed, while the rest passes further to illuminate the sample.

In an embodiment the estimate of the transmission parameter is used in a tomographic computation of an acoustic generation strength image of the sample from the acoustic signal generated inside the sample (also called the thermoacoustic image). As one example an estimated sound speed as a function of position may be used to compute a line or surface in the sample from which sound reaches a detection position at the same time, the line or surface being used in the tomographic computation to compute acoustic generation strength at positions on the line or surface. As another example estimated attenuation as a function of position may be used to correct the measured acoustic generation strength. In this case estimated attenuation as a function of position may be used to compute compound attenuation of sound between the detection position and different positions on such a computed line or surface (computed with or without using the estimated position dependent sound speed), the received signal for the line or surface being attributed to different positions on the line or surface with weights determined according to the computed compound attenuation.

By using a radiation responsive acoustic generator excited by the same type of radiation source that is used to irradiate the sample a simple set up is realized. In an embodiment this generator and the provisions for performing the accompanying computations can simply be added to an existing thermoacoustic imaging apparatus that does not provide for the estimation of a position dependent acoustic transmission parameter.

In an embodiment the speed of sound is computed in a series of iterations, wherein acoustic propagation paths are computed from the speed of sound as a function of position in the sample area computed in a previous iteration. Thus a more accurate estimate of the speed of sound distribution can be obtained.

In an embodiment responses to a common pulse of the radiation are used both in the measurement of the acoustic transmission parameter and in the measurement of the distribution of acoustic signal generation strength within the sample. This reduces the necessary number of measurements. In an alternative, separate pulses may be used.

In an embodiment the radiation responsive acoustic generator and the sample area are located successively between an output of the radiation source and an acoustic detection probe arrangement. Thus it is easily ensured that acoustic signals generated by the radiation responsive acoustic generator travels through the sample to the acoustic detection probe arrangement. This can be termed a "forward detection mode".

A "backward detection mode" is also possible with the acoustic detector located at the same side as the radiation source with respect to the sample. In such a case an acoustic mirror may be used to reflect acoustic signals from the radiation responsive acoustic generator through the sample area to the acoustic detection probe arrangement. Thus measurement of speed of sound can also be added to configurations wherein the acoustic detection probe arrangement and the radiation source are not at opposite sides of the sample.

BRIEF DESCRIPTION OF THE DRAWINGS

These and other objects and advantageous aspects will become apparent from a description of exemplary embodiments using the following figures.

DETAILED DESCRIPTION OF THE DRAWINGS

Figure 1:
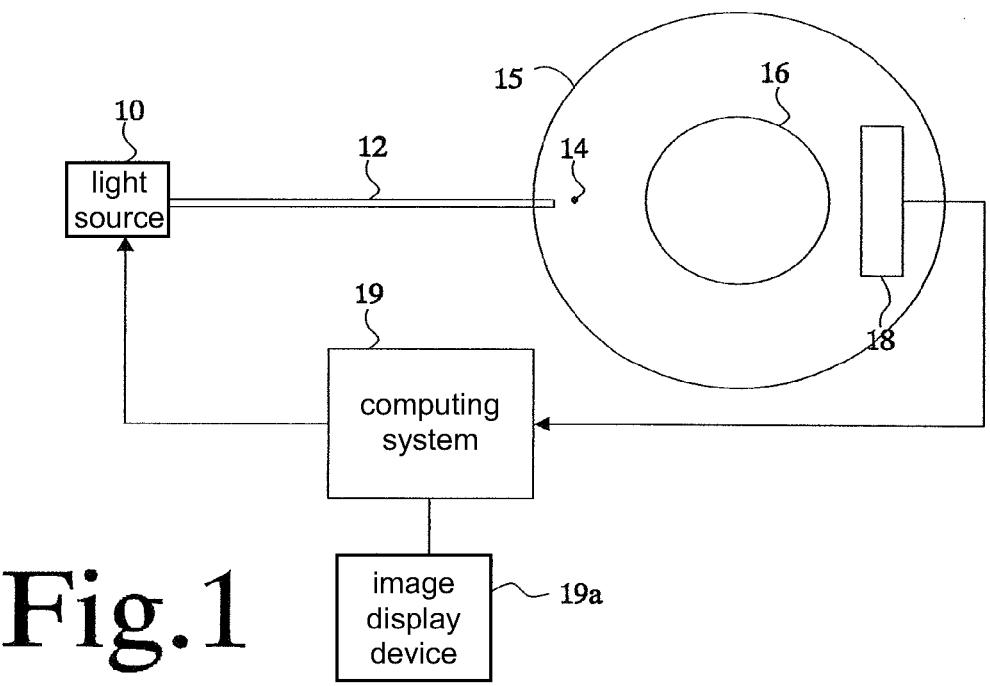
FIG. 1 shows a thermoacoustic imaging apparatus.

FIG. 1 shows a thermoacoustic imaging apparatus comprising a light source 10, a bundle of optical fibres 12, an imaging tank 15, a carbon fibre 14 a sample area 16, an ultrasound probe 18 and a computing system 19. Carbon fibre 14 and a sample area 16 are located inside imaging tank 15. The bundle of optical fibres 12 is coupled between light source 10 and sample area 16. Sample area 16 is located between the output of optical fibres 12 and ultrasound probe 18. Carbon fibre 14 is located in front of the output of optical fibres 12 between the output of optical fibres 12 and sample area 16. Ultrasound probe 18 is of a type known per se, which is configured to measure acoustic pressures as a function of position along two dimensions on the surface of ultrasound probe 18. Instead of an ultrasound probe another type of acoustic detection probe may be used.

Computing system 19 is coupled to light source 10 and ultrasound probe 18. In an embodiment, computing system 19 comprises a programmed circuit with a program for causing the circuit to perform operations described in the following, or a circuit that is hardwired to do so. As used herein the term "circuit" includes both such hardwired circuits and programmed programmable circuits. An optional image display device 19a is shown coupled to computing system 19.

In operation an acoustic coupling medium, such as water or an ultrasound gel is introduced in imaging tank 15, so that both the sample and carbon fibre 14 are immersed in the acoustic coupling medium. A sample, such as a human body part is inserted in the sample area. System 19 controls light source 10 to emit pulses of light. Optical fibres 12 transmit the light pulses to its output, from where they are transmitted to carbon fibre 14 and sample area 16. As a result of the photoacoustic effect, which is known per se, carbon fibre 14 and a sample in sample area 16 generate acoustic signals in response to light pulses. The generated acoustic signals typically are a sum of signals due to locally generate acoustic pulses. The generated acoustic signals propagate to ultrasound probe 18, which detects the resulting acoustic pressure in a two dimensional area of positions.

Computing system 19 uses measurements of the acoustic signals generated in sample area 16 to compute an acoustic generation strength image of sample area 16. The resulting image can be a three-dimensional image of the strength of generated acoustic energy as a function of the three dimensional position in sample area 16 where the acoustic pulses are generated or a two-dimensional image for example of a slice through the sample. The acoustic generation strength image is considered to be representative of an image of optical absorptivity. One may also consider a one-dimensional image of acoustic generation strength as a function of position along a path in sample area (or summed acoustic generation strength of positions on successive surfaces transverse to such a path as a function of position along the path). The estimated acoustic generation strength as a function of position may be further processed to generate the images, e.g. to emphasize certain aspects, add false color, generate synthetic views etc. The images may be displayed on image display device 19a, but they may also be used to estimate parameters such as the volume of segments having selected acoustic generation strength properties, without a need to display the image.

Methods of computing such images are known per se. The underlying principle is that acoustic pulse generation at respective locations in sample area 16 results in acoustic signals at the measuring positions on ultrasound probe 18, with time delays determined by the time needed for the acoustic pulses to travel from the location in sample area 16 to the respective measuring positions on ultrasound probe 18. The distance from the measuring position to the location in sample area can be inferred from the delay between the instant when the optical pulses illuminate the radiation responsive acoustic pulse generator and sample, to the instant of acoustic pulse reception at positions on the ultrasound probe 18. However, the signal measured at a measuring position is an average result of acoustic energy generated on a surface of locations (or line of locations, if the irradiation with light is concentrated in a plane).

To resolve acoustic generation strength as a function of location in the sample a tomographic computation is used. Techniques for performing tomographic computations are known per se. Tomography is applied in x-ray tomography for example.

The starting point of a tomographic computation is a set of measurements that each provide an average signal value along a respective surface (or line) through a sample. In a tomographic computation several measurements are used, for respective surfaces (or lines). The result of a tomographic computation is a set of estimates of the signal value as a function of estimation location in the sample. Such an estimate can be computed when measurements of the averages are available are provided for a sufficiently large set of surfaces (or lines). Preferably the set of surfaces (or lines) includes, for each estimation location, surfaces (or lines) that intersect each other at the estimation position from different directions. A sum of the measurements for these surface (or lines) is indicative of the signal value at the estimation position.

However a tomographic computation may involve more involved methods of computing the signal value. The average signal values may be projected back into image space along the lines or surfaces after filtering to minimize blurring. Performing this for all lines or surfaces, and summing the results an image is built up. This is also called filtered backprojection. Other more sophisticated methods are discussed U.S. Pat. No. 6,216,025.

In both X-ray and thermoacoustic imaging, a tomographic computation can be used to estimate signal values (X-ray absorption and acoustic signal generation strength respectively) as a function of estimation position. In the case of x-ray tomography the average signals are each a projection of absorption contributions in lines from the x-ray source to x-ray detectors. In the case of thermoacoustic imaging the average signals are average acoustic signal generation strengths for surfaces at a constant acoustic distance from positions on ultrasound probe 18. In other words, in thermoacoustic imaging arrival time of the acoustic signals resolves locations in sample area 16 along the direction towards the output of optical fibre 12.

If it may be assumed that the speed of sound in sample area does not depend on position, these surfaces would be spherical in the case of three-dimensions and circular in the case of two-dimensions. In the present apparatus surfaces that deviate from spherical surfaces are used, with a shape computed using an estimated speed of sound as a function of location in sample area 16.

In the case of one-dimensional images tomography is very simple: the signal as a function of arrival time simply corresponds to acoustic signal generation strength as a function of location, with a time dependent factor that relates time to location according to the average speed of sound at locations along a partial path between the location and ultrasound probe 18. In the higher dimensional case, a more complex computation is used to reconstruct the acoustic signal generation strength as a function of location.

In an embodiment a linear array of optical fibres 12 is provided, configured to transmit light substantially in respective planes (i.e. with an intensity distribution over a wide angle in a first spatial plane and over a much narrower angle in a second spatial plane transverse to the first spatial plane). In this embodiment light pulses being transmitted from different optical fibres 12 successively so that successive slices of sample area 16 are lighted successively and acoustic signals from the successive slices are detected successively. In another embodiment a single fibre may be used instead of fibre bundle 12, or a laser beam may be used without any fibre to direct light at carbon fibre 16 and sample area 18. A lens may be used to spread the light from the laser, fibre or fibres over sample area 18.

To determine distances from delays the computation of an image of sample area 16 requires information about the speed of sound in sample area 16. The speed of sound defines the surface in sample area 16 from which acoustic signals arrive at the same time at a position on ultrasound probe 18. In conventional methods of computation it is assumed that the speed of sound in sample area 16 is location independent. At most the average speed of sound is estimated in order to determine the distance of the surfaces to ultrasound probe 18. This has the effect that the image may be blurred if the speed of sound varies as a function of position.

In the present system the speed of sound as a function of position for use in image computation is estimated from measurements of the time of arrival of acoustic signals received due to light induced acoustic signal generation by carbon fibre 14. These estimations are used to define the surfaces in sample area 16 from which signals arrive at the same time at a position on ultrasound probe 18. Due to location dependence of the speed of sound these surfaces may deviate from spherical/circular surfaces.

Because of the difference between the speed of light and the speed of sound, at each position on ultrasound probe 18 acoustic signals generated by the sample in response to the light pulse will reach the position before acoustic signals generated in response to the light pulse by carbon fibre 14 reaches the position. Ultrasound probe 18 detects the generated acoustic signals and transmits the results of detection to computing system 19. In an embodiment a data acquisition system (not shown) may be used between ultrasound probe 18 and computing system. The acoustic signals from carbon fibre 14 can be distinguished from the acoustic signals generated by the sample by their arrival in a later time window after the light pulse. The acoustic signals in an earlier time window after the light pulse is due to acoustic signals generated by the sample.

Computing system 19 performs a tomographic computation using measurements of the acoustic signals received due to acoustic signal generation carbon fibre 14 to compute the speed of sound as a function of position in the sample in sample area 16. In a simple approximation acoustic signals generated by carbon fibre 14 reach each position on ultrasound probe 18 with a delay corresponding to the length of the acoustic path from carbon fibre 14 to that position and the average speed of sound along that path. Thus the time of arrival of the acoustic signal from carbon fibre 14 at a position on ultrasound probe 18 is indicative of the speed of sound along the path from carbon fibre 14 to the position on ultrasound probe 18. From average speed of sound the speed of sound as a function of position in sample area 16 can be computed with a tomographic computation. The geometry involved in this tomographic computation is similar to that of a fan-beam x-ray measurement, with speed of sound along a path instead of x-ray absorption.

In an embodiment, therefore, computing system 19 performs the following steps. In a first step each measuring position on ultrasound probe 18 is associated with a respective path part through sample area 16, and path parts from carbon fibre 14 to sample area 16 and from sample area 16 to ultrasound probe 18.

Figure 2:
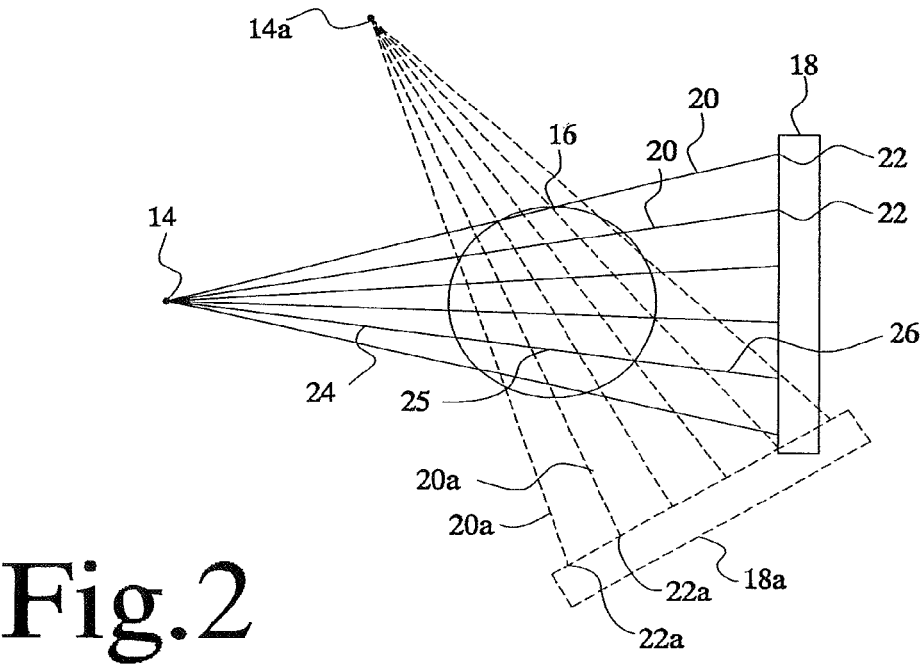
FIG. 2 shows acoustic paths through a sample area

FIG. 2 shows an example of acoustic paths 20 associated with positions 22 on ultrasound probe 18. When the speed of sound is substantially the same in all path parts 24, 25, 26 straight paths 20 from carbon fibre 14 to different measuring points on ultrasound probe 18 may be used. If the speeds of sound in different path parts are different refracted paths may be used. In a third step computing system 19 measures the delay between the light pulse and reception of acoustic signal generated by carbon fibre 14 at the respective measuring positions, and divides the path length for the positions by the measured delays to obtain the average speed of sound along the path. Optionally, known delays for the path parts outside sample area 16 are subtracted first and the length of the path part in sample area divided by the remaining delay is computed.

In a further embodiment a reference measurement without a sample is also performed, for example with only acoustic coupling medium and carbon fibre 16 in imaging tank 19, or with a standard reference sample. In this embodiment the change in average speed is determined from a difference between the time of arrival of acoustic signal attributed to carbon fibre 16 with and without the presence of the sample. For every position on the ultrasound probe 18, the acoustic signal responses obtained with and without the sample are cross-correlated. The time delay difference between the situation without the sample and with the sample is obtained at the point where the cross-correlation function is a maximum.

In a further embodiment, before correlation the envelope of the acoustic signal responses may also be calculated by computing the Hilbert transformation, of the detected acoustic signal and taking the absolute value of the Hilbert transform prior to cross-correlation. This increases the accuracy of the time-delay estimation.

In the embodiment with cross-correlation, measurements or images of speed of sound computed are relative to the speed of sound in the coupling medium. Here it is then preferable to use a medium with well characterized acoustic properties such as degassed and demineralised water. As used herein, when a detection of determination of sound speed and speed of sound are referred to, this will be taken to cover also detection or determination of change in sound speed, or difference between sound speed with and without the presence of the sample.

In an embodiment some or all of the previously described steps are repeated with sample area 16 at a series of different orientations relative to optical fibre 12, carbon fibre 14 and ultrasound probe 18, preferably keeping the same relative position of optical fibre 12, carbon fibre 14 and ultrasound probe 18 with respect to each other.

FIG. 2 shows the paths 20*a* from carbon fibre 14*a* associated with positions 22*a* on an ultrasound probe 18*a* with carbon fibre 14*a* and ultrasound probe 18*a* under a different orientation. From the measurements at different orientations average sound speeds (or changes in sound speed due to the sample) along sets of paths 20, 20*a* along different orientations are obtained. From such sets average sound speeds (or changes in sound speed due to the sample) for a plurality of sets of paths along different orientations the sound speed (or change in sound speed due to the sample) as a function of position is estimated.

Any tomographic computation technique may be used, for example as described in the preceding. The tomographic computation can be similar to that used for fan-beam x-ray tomography, using sound speed (or change in sound speed due to the sample) instead of x-ray absorption. As such computation techniques are known per se they will not be described in detail.

In this tomographic computation assumed acoustic paths 20, 20*a* are used. In a first approximation acoustic paths 20, 20*a* that run straight through sample area 16 may be used in the tomographic computation. However, if the speed of sound varies with position, refraction may occur, which introduces errors because the actual acoustic path from carbon fibre 14 through sample area 16 will not be straight. In an embodiment a correction is made for refraction by iterating the tomographic computation of the speed of sound, each iteration using acoustic paths computed using the position dependent speed of sound computed in the previous iteration. It should be noted that the iterations do not require new measurements: only the computation of speeds of sound from the old measurements needs to be repeated with successively different paths.

The embodiments described above apply to the case where propagation of the generated acoustic pulses may be approximated by a set of rays, i.e. for short wavelength acoustic pulses. A different computation may be used when wave effects cannot be completely neglected.

In the embodiment wherein the light is emitted spread over directions in a first plane with a narrow distribution transverse to that first plane, carbon fibre 14 is provided with its length extending transverse to the first planes, so that each optical fibre 12 will light only a small section of carbon fibre 14. In an embodiment, for each light pulse only acoustic signal measurements from measurement positions on ultrasound probe 18 in the first plane wherein the light pulse was transmitted may be used to compute the speed of sound. Thus a lower dimensional and therefore faster sound speed reconstruction algorithm suffices. Also, light pulses and measurements may be applied only to one or a few planes if investigation of this plane or these planes suffices for diagnostic purposes. Alternatively ultrasound probe 18 may be used to detect acoustic pulses generated from different sections of the bundle optical fibre 12 separately, each in two dimensions to obtain average speeds along paths in different crossing sets of paths. Thus more paths are available for computing the speed of sound as a function of position.

In the described embodiments light pulses from optical fibres 12 are used both for providing measurements for a first computation of sound speed as a function of position in sample area 16 and for a second computation of acoustic signal generation strength as a function of position in sample area 16. Preferably both the first and second computation use measurements in response to the same light pulse or pulses. Alternatively, measurements in response to separate light pulses may be used for the first and second computation respectively. Using measurements in response to the same light pulse or pulses has the advantage that fewer measurements are needed and that there is less sensitivity to movement in sample area 16.

The speed of sound as a function of position that has been computed in this way is used to compute the shape of a surface (or line) of locations from which acoustic pulses generated in sample area 16 reach a position on ultrasound probe at the same time. A plurality of surfaces (or lines) that are determined in this way is subsequently used in the tomographic computation of the acoustic generation strength.

In the tomographic computation of images of acoustic generation strength or thermoacoustic images of the sample using an assumed constant speed of sound, as mentioned earlier, filtered backprojection is used where the backprojection of measured acoustic signals (with time axis converted into a distance axis) is performed in circular or spherical surfaces into image space. In order to correct such images the spatial variation of speed of sound in the sample obtained from the computed speed of sound image is used. The extent of the distortion of the circular or spherical surfaces is determined by integrating weighted values of the speed of sound image encountered along paths from the radiation responsive acoustic pulse generator to the appropriate part of the ultrasound probe. The circular or spherical surfaces are then advanced or retarded appropriately along those paths.

A tomographic computation is then performed along these distorted circular or spherical surfaces to give the thermoacoustic image corrected for the spatial variation in speed of sound as obtained from the computed speed of sound image.

Although an embodiment has been described wherein an ultrasound probe 18 is used that is capable of simultaneously detecting acoustic signal at a number of measurement positions it should be appreciated that alternatively a probe may be used that detects acoustic signal only at a single position. By scanning such a probe more measurements may be obtained. Also, although a single ultrasonic probe 18 has been shown it should be appreciated that an probe arrangement with one or more probes may be used, for example comprising separate probes for the determination of the speed of sound and the acoustic generation strength image. Also although a rectilinear probe has been shown, a curvilinear probe may be used. Further cylindrical or hemispherical probes may also be used.

Although an embodiment has been described wherein a carbon fibre 14 is used as a radiation responsive acoustic source for the determination of the speed of sound, it should be appreciated that different materials, or differently shaped sources may be used. It suffices that the material passively generates acoustic pulses in response to light pulses, without requiring additional excitation means that are not needed for the thermoacoustic measurement itself. A source that has a point like cross-section, such as a fibre may be used. This simplifies computations. Alternatively a differently shaped source that provides a predetermined acoustic generation pattern as a function of position may also be used, for example an array of carbon fibres. This may be accounted for in the computation of the speed of sound.

Although an embodiment has been described wherein light is used to generate the acoustic signal in sample area 16 and carbon fibre 14, it should be appreciated that alternatively different radiation may be used, such as microwave radiation, radiofrequency waves, x-rays etc. In an embodiment a laser with a wavelength in the UV, visible or infrared wavelength regions is used, or light pulses from a Xenon flashlamp may be used.

Of course, when a different type of radiation is used, carbon fibre 14 may be replaced by another material that is suitable for use with the particular type of radiation.

Although an embodiment has been described wherein pulses of light are used, it should be appreciated that alternatively other types of time dependent radiation may be used to generate the acoustic signal.

It should be emphasized that the computation of sound speed may be provided for as an add-on for any apparatus for determining acoustic generation strength as a function of position in a sample area that does not yet provide for the determination of position dependent sound speed. In principle it suffices to add a radiation responsive acoustic signal source such as carbon fibre 14, a program for separating acoustic signal due to sample area 16 and acoustic signal due to the added radiation responsive acoustic signal source, and a program for computing sound speed from the sound due to the added radiation responsive acoustic signal source.

A preferred embodiment has been shown wherein sample area 16 is located between the output of the optical fibre 12 and ultrasound probe 18 and wherein sample area 16 is located between the radiation responsive acoustic signal source and the ultrasound probe 18, so that acoustic signal travels from the radiation responsive acoustic signal source to the ultrasound probe via sample area 16. However it should be appreciated that other arrangements may be used. For example, sample area 16 need not be located between the output of the optical fibre 12 and ultrasound probe. In this case the radiation responsive acoustic signal source may be provided on a side of sample area 16 opposite ultrasound probe 18.

Figure 3:
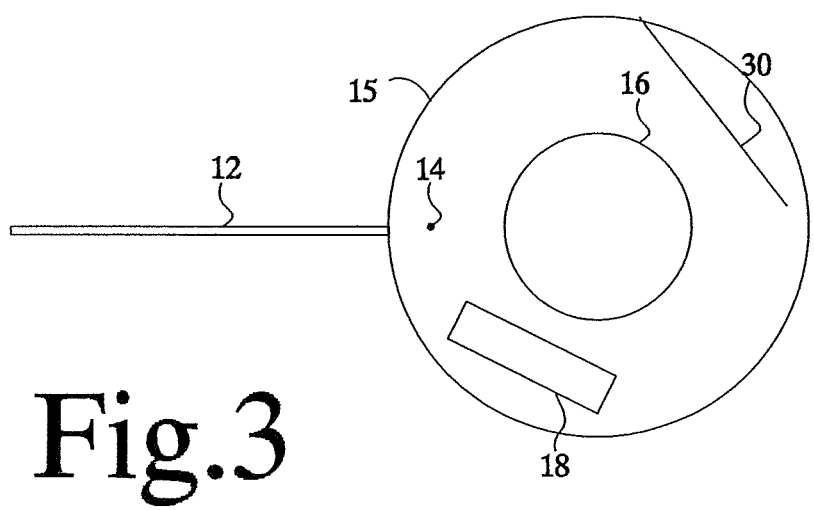
FIG. 3 shows an alternative arrangement of a thermoacoustic imaging apparatus.

FIG. 3 shows an alternative wherein the radiation responsive acoustic signal source is provided between the output of the optical fibre 12 and sample area 16 and an acoustic signal mirror 30 is provided to reflect acoustic signals from radiation responsive acoustic signal source to ultrasound probe 18 through sample area 16.

Although embodiments have been shown wherein the estimated speed of sound is used to improve the acoustic generation strength image, it should be understood that the estimated sound speed distribution may also be used to generate sound speed images that can be useful for diagnostic medical purposes by themselves, or in combination with the acoustic generation strength image.

In a further embodiment attenuation of sound as a function of position in the sample may also be estimated. The estimated attenuation may be used to improve the acoustic generation strength image by applying a correction for the attenuation, or attenuation on its own may be used, without computing the acoustic generation strength image. The attenuation as a function of position may be estimated in a similar way as the speed of sound as a function of position, using measurements of received acoustic signal strength from radiation responsive acoustic pulse generator instead of time delay of the received acoustic signal. In an embodiment, the amplitudes of the acoustic pulses generated by carbon fibre 16 at positions at ultrasound probe 18 are measured with and without the sample in the coupling medium. In the measurement without the sample a medium with well characterized acoustic properties such as degassed and demineralised water is preferably used In an embodiment the method of calculation of the relative acoustic attenuation along a certain acoustic propagation path is performed by taking the ratio of the peak values or the total energies in the acoustic pulses from the carbon fiber received at a certain position of the ultrasound probe, with and without the sample in the coupling medium. This is a measure of the acoustic attenuation through the acoustic path through the sample relative to the coupling medium.

However, this method however is sensitive to transmission losses due to reflections at the coupling medium-sample interfaces and may result in an overestimation of the attenuation. Another method is to use the frequency-shift method described by A. C. Kak and K. A. Dines in their article "Signal processing of broadband pulsed ultrasound: measurement of attenuation of soft biological tissues", published in the IEEE Transactions on Biomedical Engineering (1978) July; 25(4), pp. 321-44. Herein they use the measurement of the frequency shifts in the central frequencies of the received acoustic pulses with and without sample in coupling medium to estimate the relative acoustic attenuation. This method is insensitive to reflection losses and can yield a more accurate estimation of the relative acoustic attenuation. It must be appreciated that knowing the acoustic attenuation of the coupling medium the attenuation of the sample may be calculated.

In an alternative embodiment absolute attenuation is computed from a measurement with the sample present without using a reference measurement without the sample. As another alternative a relative attenuation relative to default reference may be used, which has been computed without actual measurement.

In the same way as the speed of sound can be determined as a function of position from the time of arrival, the attenuation as a function of position can be determined from the detected average attenuation. These measurements or images of acoustic or relative acoustic attenuations are useful in themselves for diagnostic purposes but also for correcting the thermoacoustic images developed.

In another embodiment only a measurement in the presence of the sample is used. In this case the detected peak signal strength of acoustic pulses from carbon fibre 14 at the end of different acoustic pulse paths from carbon fibre 14, divided by a predetermined reference value may be used in a tomographic computation of attenuation.

The correction of the acoustic strength generation image for attenuation may also be performed. As mentioned earlier the thermoacoustic image of the sample is developed by tomographic computation of the measured acoustic signals. In such cases the backprojection may be performed without any amplitude weighting of backprojected signals. An embodiment wherein corrections for the spatial variation of acoustic attenuation are performed will now be described. The integrated acoustic attenuation at a point is calculated for each point along the acoustic path from the radiation responsive acoustic pulse generator to the appropriate part of the ultrasound probe. By integrated acoustic attenuation at a point is meant that the value at any point is the summation of all acoustic attenuation values encountered along the acoustic path till that point. The part of the acoustically backprojected circular or spherical surface or distorted circular or spherical surface passing through this point is then weighted inversely with this integrated value. Thus, the backprojected value for each point on the line or surface is computed according to the signal generation strength that would have to occur at the points to create equal contributions from all points at the detection position, after undergoing the respective computed attenuations from the respective points to the detection position.

In a further embodiment both the speed of sound and the acoustic attenuation may be estimated in addition to the thermoacoustic image. This in the simplest model will consist in examining the acoustic pulses generated by carbon fibre 16 with and without the sample in the coupling medium. In such a situation the computing system is so configured as to analyze the acoustic pulses generated by the carbon fibre for both (relative) time-delays as well as for (relative) acoustic attenuation with respect to the well-characterized coupling medium.

The invention claimed is:

1. An imaging apparatus, comprising
an electromagnetic radiation source;
a radiation responsive acoustic signal generator located outside a sample area being irradiated by the electromagnetic radiation source, wherein the radiation responsive acoustic signal generator is made of a material that generates acoustic signals by photoacoustic effect in response to electromagnetic irradiation from the electromagnetic radiation source;
an acoustic signal detection probe arrangement for detecting acoustic signals generated in the sample area in response to the irradiation and for detecting an acoustic signal from the radiation responsive acoustic signal generator that has travelled through the sample area;
a computing system configured to:
distinguish first acoustic signal detections attributed to the acoustic signal generated by the radiation responsive acoustic signal generator and second acoustic signal detections attributed to the acoustic signals generated by the sample area;
perform, from the first acoustic signal detections, a tomographic computation of an acoustic transmission parameter as a function of position in the sample area.

2. An imaging apparatus of claim 1 wherein the computing system is configured to perform a tomographic computation of an acoustic generation strength image of the sample from the second acoustic signal detections, using the position dependent acoustic transmission parameter computed from the first detections.

3. An imaging apparatus according to claim 1, wherein the acoustic transmission parameter is a speed of sound as a function of position.

4. An imaging apparatus according to claim 3, wherein the computing system is configured to compute the speed of sound in a series of iterations, each iteration comprising computing average sound speeds through respective acoustic paths through the sample area, the acoustic paths in all but the first iteration being computed from the speed of sound as a function of position in the sample area computed in a previous iteration.

5. A imaging apparatus according to claim 1, wherein the computing system is configured to compute attenuation of acoustic signals as a function of a position in the sample area from the first acoustic signal detections.

6. A imaging apparatus according to claim 5, wherein the computing system is configured to compute the acoustic generation strength image of the sample from the second acoustic signal detections using the position dependent attenuation of acoustic signals computed from the first acoustic signal detections.

7. An imaging apparatus according to claim 1, wherein the computing system is configured to obtain the first and second acoustic signal detections both in response to a common pulse of the radiation.

8. An imaging apparatus according to claim 1, wherein radiation source is a light source and the radiation responsive acoustic signal generator is a carbon fibre, a coloured nylon fibre, or a strand of black human or animal hair.

9. An imaging apparatus according to claim 1, wherein the sample area is located between an output of the radiation source and the acoustic signal detection probe arrangement and wherein the radiation responsive acoustic signal generator is located between the output of the radiation source and the sample area.

10. An imaging apparatus according to claim 1, further comprising an acoustic signal mirror configured to reflect acoustic signals from the radiation responsive acoustic signal generator through the sample area to the acoustic signal detection probe arrangement.

11. An imaging apparatus according to claim 1, wherein the computing system is configured to compute position dependent acoustic attenuation in the sample by comparing amplitudes of the first acoustic signal detections to previously obtained reference acoustic detections.

12. An imaging apparatus according to claim 1, wherein the computing system is configured to compute a difference between a speed of sound with the sample and a speed of sound without the sample by comparing the first acoustic signal detections to previously obtained reference acoustic signal detections, the previously obtained reference acoustic signal detections having been obtained without the sample.

13. A method of forming an image, the method comprising
irradiating a sample with electromagnetic radiation that causes acoustic signals to be generated in the sample in response to the radiation;

providing a radiation responsive acoustic signal generator outside the sample wherein the radiation responsive acoustic signal generator is made of a material that generates acoustic signals by photoacoustic effect in response to electromagnetic irradiation from the electromagnetic radiation source;

detecting acoustic signals generated by the sample and the radiation responsive acoustic signal generator that have propagated through the sample;

distinguishing first acoustic signal detections due to the acoustic signal generated by the radiation responsive acoustic signal generator and second acoustic signal detections due to the acoustic signals generated by the sample, performing a tomographic computation of values of an acoustic transmission parameter of the sample as a function of a position in the sample from the first acoustic signal detections.

14. A method according to claim 13, comprising performing a tomographic computation of an acoustic signal generation strength image of the sample from the second acoustic signal detections using the position dependent speed of the acoustic transmission parameter computed from the first detections.

15. A method according to claim 13, the method comprising providing an acoustic coupling medium between a source of the irradiation and a detector for the acoustic signals, the radiation responsive acoustic signal generator and the sample being provided both immersed in the acoustic coupling medium.

16. A method according to claim 13, the method further comprising:

performing a reference measurement by irradiating a sample area for the sample in the absence of the sample in that sample area, but with the radiation responsive acoustic signal generator and detecting acoustic signal generated by the radiation responsive acoustic signal generator;

comparing the first acoustic signal detections results obtained with the sample in the sample area with detection results obtained without the sample in the sample area.

17. A method according to claim 13, the method comprising computing speed of sound as a function of a position in the sample area from the first acoustic signal detections.

18. A method according to claim 17, comprising computing the acoustic signal generation strength image of the sample from the second acoustic signal detections using the position dependent speed of sound computed from the first acoustic signal detections.

19. A method according to claim 13, the method further comprising computing attenuation of acoustic signal as a function of a position in the sample area from the first acoustic signal detections.

20. A method according to claim 19, the method further comprising computing the acoustic signal generation strength image of the sample from the second acoustic signal detections using the position dependent attenuation of acoustic signal computed from the first acoustic signal detections.

\* \* \* \* \*